US009055741B2

(12) United States Patent
Bardella et al.

(10) Patent No.: US 9,055,741 B2
(45) Date of Patent: Jun. 16, 2015

(54) CONTACTING CROP PLANTS WITH COMPOSITIONS

(75) Inventors: Eduardo José Bardella, Buenos Aires (AR); Richard Martin Basel, Fostoria, OH (US); David Ross Dilley, East Lansing, MI (US); Jon Frederick Fobes, Lower Gwynedd, PA (US); Edward Charles Kostansek, Buckingham, PA (US); Robert Lynn Oakes, Doylestown, PA (US); Arden Nathan Reed, Wenatchee, WA (US)

(73) Assignee: Rohm and Haas Company, Philadelphia, PA (US)

( * ) Notice: Subject to any disclaimer, the term of this patent is extended or adjusted under 35 U.S.C. 154(b) by 575 days.

(21) Appl. No.: 11/801,515

(22) Filed: May 10, 2007

(65) Prior Publication Data

US 2007/0265166 A1 Nov. 15, 2007

Related U.S. Application Data

(60) Provisional application No. 60/800,516, filed on May 15, 2006.

(51) Int. Cl.
*A01N 27/00* (2006.01)
*A01N 25/06* (2006.01)

(52) U.S. Cl.
CPC ....................................... *A01N 27/00* (2013.01)

(58) Field of Classification Search
CPC ..................................................... A01N 27/00
USPC ....................................................... 504/114
See application file for complete search history.

(56) References Cited

U.S. PATENT DOCUMENTS

| 5,518,988 | A | 5/1996 | Sisler |
| 5,834,403 | A | 11/1998 | Callan |
| 6,017,849 | A | 1/2000 | Daly |
| 6,194,350 | B1 | 2/2001 | Sisler |
| 6,357,207 | B1 | 3/2002 | Weder |
| 6,365,549 | B2 | 4/2002 | Sisler |
| 6,426,319 | B1 | 7/2002 | Kostansek |
| 6,548,448 | B2 | 4/2003 | Kostansek |
| 6,762,153 | B2 | 7/2004 | Kostansek |
| 6,953,540 | B2 | 10/2005 | Chong |
| 2001/0019995 | A1 | 9/2001 | Sisler |
| 2004/0029736 | A1 | 2/2004 | Jansen |
| 2005/0065033 | A1 | 3/2005 | Jacobson |
| 2005/0261131 | A1 | 11/2005 | Basel |
| 2005/0261132 | A1 | 11/2005 | Kostansek |
| 2005/0288189 | A1 | 12/2005 | Jacobson |
| 2006/0160704 | A1 | 7/2006 | Basel |
| 2007/0093389 | A1 | 4/2007 | Rademacher |
| 2007/0149401 | A1 | 6/2007 | Haskell |
| 2007/0199242 | A1 | 8/2007 | Hansen |

FOREIGN PATENT DOCUMENTS

| EP | 1 680 960 A1 | 7/2006 |
| EP | 07251871 | 1/2013 |
| RU | 2267477 | 1/2006 |
| WO | WO 2005/044002 | 5/2005 |
| WO | WO2007/001919 | 1/2007 |
| WO | WO2007/096833 | 8/2007 |
| WO | WO2007/104660 | 9/2007 |

OTHER PUBLICATIONS

Fan, X,. Development of Apple Superficial Scald, Soft Scald, Core Flush, and Greasiness Is Reduced by MCP, 1999, Journal of Agricultural and Food Chemistry, vol. 47, pp. 3063-3068.*
E.C. Sisler et. al., "Inhibition of ethylene responses by 1-methylcyclopropene and 3-methylcyclopropene", Plant Growth Regulation, vol. 27, pp. 105-111, 1999.
Jones, et al., "Role of Ethylene and 1-MCP in Flower Development and Petal Abscission in Zonal Geraniums", Horticultural Science, v. 36, No. 7, pp. 1305-1309, 2001.
R. E. Byers, et. al., "Ethylene Inhibitors Delay Fruit Drop, Maturity, and Increase Fruit Size of 'Arlet' Apples", Hortscience, Dec. 2005, pp. 2061-2065, vol. 40.
D.B. Hays, et. al., "The role of ethylene during reproductive development in wheat (*Triticum aestivum*) under . . . ", Am. Soc. of Plant Biologists Symposium, Seattle, WA, (2005).
S.M. Blankenship, et. al., "1-Methylcyclopropene: a review", Postharvest Biology and Technology, 2003, pp. 1-25, vol. 28.
R.K. Prange, et. al., "1-Methylcyclopropen: The 'magic bullet' for Horticultural Products?" Chronica Horticulturae, 2003, pp. 11-14, vol. 43.
L.F.M. Marcellis, et. al., "Flower and fruit abortion in sweet pepper in relation to source and sink strength," Journal of Experimental Biology, 2004, No. 406, pp. 2261-2268.
E.C. Sisler, et. al., "Inhibitors of ethylene responses in plants at the receptor level: Recent developments" Physiologica Plantarum, 1997, pp. 577-582, vol. 100.
R.E. Byers, et.al., "Pre Harvest Fruit Drop, Harvest Quality, and Cold Storage of 'Golden Delicious' and 'Rome' Apples," Proceedings of the Plant Growth Regulation Society of America, v.27, pp. 175-180, 2000.
Sisler, E. C. et al: "Compounds interacting with the ethylene receptor in plants", Plant Biology, Wiley-Blackwell Publishing Ltd, GB, DE, NL, vol. 5, No. 5, Sep. 1, 2003, pp. 473-480, XP002502595, ISSN: 1435-8603, DOI: 10.1055/S-2003-44782.
Greene, Duane W et al: "Effect of aminoethoxyvinylglycine (AVG) on preharvest drop, fruit quality, and maturation of 'McIntosh' Apples. II. Effect of timeing and concentration relationships and spray volume", Hortscience, vol. 39, No. 5, Aug. 2004, p. 1036, XP002689049, ISSN: 0018-5345.
Dekazos E D: "Effect of Aminoethoxyvinyl Glycine on Bloom Delay Fruit Quality and Chemical Pruning of Apple Malus-Domestica Trees", Hortscience, vol. 16, No. 3 Sect. 2, 1981, p. 455, XP002689050, ISSN: 0018-5345.

* cited by examiner

*Primary Examiner* — Sue Liu
*Assistant Examiner* — Andriae M Holt
(74) *Attorney, Agent, or Firm* — Yung H. Lee; TraskBritt, P.C.

(57) ABSTRACT

Provided are methods of treating specific crop plants when those plants have reached specific developmental stages. Also provided is a method for improving the yield of a crop produced by a plurality of plants, which may or may not be any of the specific plants mentioned herein above, wherein said method comprises contacting said plants with at least one composition that comprises at least one cyclopropene.

7 Claims, No Drawings

CONTACTING CROP PLANTS WITH COMPOSITIONS

This application claims the benefit of priority under 35 U.S.C. §119(e) of U.S. Provisional Patent Application No. 60/800,516 filed on May 15, 2006.

BACKGROUND

Plants are often treated by contacting them with compositions. For example, U.S. patent application Ser. No. 11/324,617 discloses treating non-*citrus* plants with compositions that contain at least one cyclopropene and that contain at least one plant growth regulator that is not a cyclopropene. It is desired to provide methods that involve treating certain specific crop plants at developmental stage or stages appropriate for those specific crop plants. Independently, it is also desired to provide methods of treating plants that result in an increase in the yield of the crop produced by those plants.

STATEMENT OF THE INVENTION

In a first aspect of the present invention, there is provided a method for improving the yield of a crop produced by a plurality of plants, wherein said method comprises contacting said plants with at least one composition that comprises at least one cyclopropene, with the proviso that when said plants comprise apple trees, each of said compositions contains no aminoethoxyvinylglycine, wherein said contacting is performed while said plants are in a location other than in a building.

In a second aspect of the present invention, there is provided a method of treating corn plants comprising at least one step of contacting said corn plants one or more times with at least one liquid composition comprising at least one cyclopropene, wherein at least one of said contacting steps is conducted after at least 10% of said corn plants have reached the developmental stage at which the fifth leaf is fully expanded.

In a third aspect of the present invention, there is provided a method of treating cotton plants comprising at least one step of contacting said cotton plants one or more times with at least one liquid composition comprising at least one cyclopropene, wherein at least one of said contacting steps is conducted after at least 10% of said cotton plants have undergone seedling emergence.

In a fourth aspect of the present invention, there is provided a method of treating soybean plants comprising at least one step of contacting said soybean plants with at least one liquid composition comprising at least one cyclopropene, wherein at least one of said contacting steps is conducted after at least 10% of said soybean plants have at least one node on the main stem with at least one fully developed leaf.

In a fifth aspect of the present invention, there is provided a method of treating oilseed rape plants comprising at least one step of contacting said oilseed rape plants with at least one liquid composition comprising at least one cyclopropene, wherein at least one of said contacting steps is conducted after at least 10% of said oilseed rape plants have begun to bloom.

In a sixth aspect of the present invention, there is provided a method of treating wheat plants comprising at least one step of contacting said wheat plants with at least one liquid composition comprising at least one cyclopropene, wherein at least one of said contacting steps is conducted during F9.0 growth stage of said wheat plants.

DETAILED DESCRIPTION

The practice of the present invention involves the use of one or more cyclopropenes. As used herein, "cyclopropene" means any compound with the formula

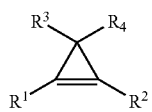

where each $R^1$, $R^2$, $R^3$ and $R^4$ is independently selected from the group consisting of H and a chemical group of the formula:

$$-(L)_n-Z$$

where n is an integer from 0 to 12; each L is independently selected from the group consisting of D1, D2, E, and J; where D1 is of the formula:

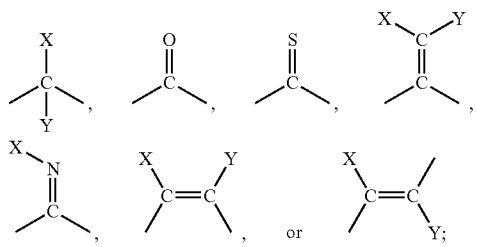

where D2 is of the formula:

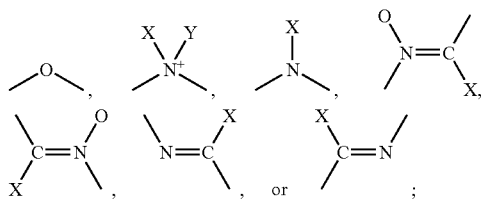

where E is of the formula:

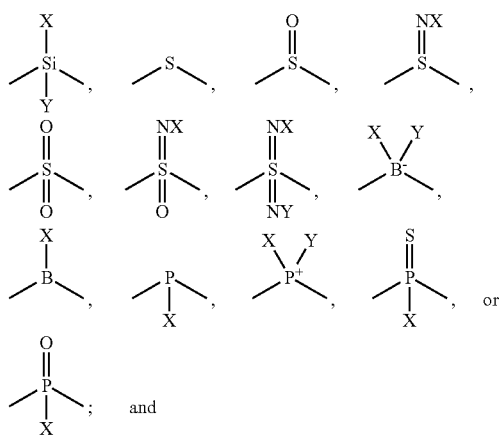

and where J is of the formula:

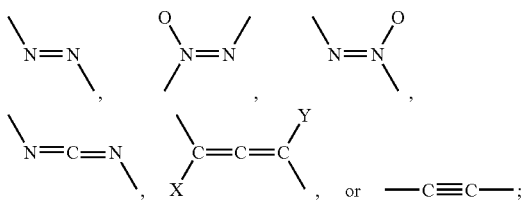

where each X and Y is independently a chemical group of the formula;

-(L)$_m$-Z;

and m is an integer from 0 to 8; and no more than two D2 or E groups are adjacent to each other and no J groups are adjacent to each other; where each Z is independently selected from the group consisting of hydrogen, halo, cyano, nitro, nitroso, azido, chlorate, bromate, iodate, isocyanato, isocyamido, isothiocyanato, pentafluorothio, and a chemical group G, wherein G is a 3 to 14 membered ring system; where the total number of heteroatoms in -(L)$_n$-Z is from 0 to 6; and where the total number of non-hydrogen atoms in the compound is 50 or less.

For the purposes of this invention, in the structural representations of the various L groups, each open bond indicates a bond to another L group, a Z group, or the cyclopropene moiety. For example, the structural representation

indicates an oxygen atom with bonds to two other atoms; it does not represent a dimethyl ether moiety.

Among embodiments in which at least one of $R^1$, $R^2$, $R^3$, and $R^4$ is not hydrogen and has more than one L group, the L groups within that particular $R^1$, $R^2$, $R^3$, or $R^4$ group may be the same as the other L groups within that same $R^1$, $R^2$, $R^3$, or $R^4$ group, or any number of L groups within that particular $R^1$, $R^2$, $R^3$, or $R^4$ group may be different from the other L groups within that same $R^1$, $R^2$, $R^3$, or $R^4$ group.

Among embodiments in which at least one of $R^1$, $R^2$, $R^3$, and $R^4$ contains more than one Z group, the Z groups within that $R^1$, $R^2$, $R^3$, or $R^4$ group may be the same as the other Z groups within that $R^1$, $R^2$, $R^3$, or $R^4$ group, or any number of Z groups within that $R^1$, $R^2$, $R^3$, or $R^4$ group may be different from the other Z groups within that $R^1$, $R^2$, $R^3$, or $R^4$ group.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be substituted or unsubstituted. Some suitable substituted aliphatic groups include, for example, acetylaminoalkenyl, acetylaminoalkyl, acetylaminoalkynyl, alkoxyalkoxyalkyl, alkoxyalkenyl, alkoxyalkyl, alkoxyalkynyl, alkoxycarbonylalkenyl, alkoxycarbonylalkyl, alkoxycarbonylalkynyl, alkylcarbonyloxyalkyl, alkyl(alkoxyimino)alkyl, carboxyalkenyl, carboxyalkyl, carboxyalkynyl, haloalkoxyalkenyl, haloalkoxyalkyl, haloalkoxyalkynyl, haloalkenyl, haloalkyl, haloalkynyl, hydroxyalkenyl, hydroxyalkyl, hydroxyalkynyl, trialkylsilylalkenyl, trialkylsilylalkyl, trialkylsilylalkynyl, dialkylaminoalkyl, alkylsulfonylalkyl, alkylthioalkenyl, alkylthioalkyl, alkylthioalkynyl, haloalkylthioalkenyl, haloalkylthioalkyl, and haloalkylthioalkynyl.

Also among the suitable $R^1$, $R^2$, $R^3$, and $R^4$ groups are, for example, substituted and unsubstituted aliphatic-oxy groups, such as, for example, alkenoxy, alkoxy, alkynoxy, and alkoxycarbonyloxy.

Also among the suitable $R^1$, $R^2$, $R^3$, and $R^4$ groups are, for example, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, for example, alkylphosphonato, dialkylphosphato, dialkylthiophosphato, dialkylamino, alkylcarbonyl, and dialkylaminosulfonyl.

Among the aliphatic groups suitable as $R^1$, $R^2$, $R^3$, or $R^4$ are, for example, cycloaliphatic groups, including, for example, cycloalkenyl, cycloalkyl, and cycloalkynyl. Suitable cycloaliphatic groups may be substituted or unsubstituted. Among the suitable substituted cycloaliphatic groups are, for example, acetylaminocycloalkenyl, acetylaminocycloalkyl, acetylaminocycloalkynyl, cycloalkenoxy, cycloalkoxy, cycloalkynoxy, alkoxyalkoxycycloalkyl, alkoxycycloalkenyl, alkoxycycloalkyl, alkoxycycloalkynyl, alkoxycarbonylcycloalkenyl, alkoxycarbonylcycloalkyl, alkoxycarbonylcycloalkynyl, cycloalkylcarbonyl, alkylcarbonyloxycycloalkyl, carboxycycloalkenyl, carboxycycloalkyl, carboxycycloalkynyl, halocycloalkoxycycloalkenyl, halocycloalkoxycycloalkyl, halocycloalkoxycycloalkynyl, halocycloalkenyl, halocycloalkyl, halocycloalkynyl, hydroxycycloalkenyl, hydroxycycloalkyl, hydroxycycloalkynyl, trialkylsilylcycloalkenyl, trialkylsilylcycloalkyl, trialkylsilylcycloalkynyl, dialkylaminocycloalkyl, alkylsulfonylcycloalkyl, cycloalkylcarbonyloxyalkyl, cycloalkylsulfonylalkyl, alkylthiocycloalkenyl, alkylthiocycloalkyl, alkylthiocycloalkynyl, haloalkylthiocycloalkenyl, haloalkylthiocycloalkyl, and haloalkylthiocycloalkynyl.

Also among the suitable $R^1$, $R^2$, $R^3$, and $R^4$ groups are, for example, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, for example, substituted and unsubstituted heterocyclyl groups (i.e., non-aromatic cyclic groups with at least one heteroatom in the ring). Among the suitable substituted heterocyclyl groups are, for example, alkenylheterocyclyl, alkylheterocyclyl, alkynylheterocyclyl, acetylaminoheterocyclyl, alkoxyalkoxyheterocyclyl, alkoxyheterocyclyl, alkoxycarbonylheterocyclyl, alkoxycarbonyloxyheterocyclyl, carboxyheterocyclyl, haloalkoxyheterocyclyl, haloheterocyclyl, hydroxyheterocyclyl, trialkylsilylheterocyclyl, dialkylaminoheterocyclyl, alkylsulfonylheterocyclyl, alkylthioheterocyclyl, heterocyclylthioalkyl, and haloalkylthioheterocyclyl.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted aryl groups. Some suitable substituted aryl groups are, for example, alkenylaryl, alkylaryl, alkynylaryl, acetylaminoaryl, aryloxy, alkoxyalkoxyaryl, alkoxyaryl, alkoxyalkoxyaryl, alkoxycarbonylaryl, arylcarbonyl, alkylcarbonyloxyaryl, carboxyaryl, diarylamino, haloalkoxyaryl, haloaryl, hydroxyaryl, trialkylsilylaryl, dialkylaminoaryl, alkylsulfonylaryl, arylsulfonylalkyl, alkylthioaryl, arylthioalkyl, diarylaminosulfonyl, and haloalkylthioaryl.

Also among the suitable $R^1$, $R^2$, $R^3$, and $R^4$ groups are, for example, substituted and unsubstituted heteroaryl groups. Some suitable substituted heteroaryl groups are, for example, alkenylheteroaryl, alkylheteroaryl, alkynylheteroaryl, acetylaminoheteroaryl, heteroaryloxy, alkoxyalkoxyheteroaryl, alkoxyheteroaryl, alkoxycarbonylheteroaryl, heteroarylcarbonyl, alkylcarbonyloxyheteroaryl, carboxyheteroaryl, diheteroarylamino, haloalkoxyheteroaryl, haloheteroaryl, hydroxyheteroaryl, trialkylsilylheteroaryl, dialkylaminoheteroaryl, alkylsulfonylheteroaryl, heteroarylsulfonylalkyl, alkylthioheteroaryl, and haloalkylthioheteroaryl.

Also among the suitable $R^1$, $R^2$, $R^3$, and $R^4$ groups are, for example, substituted and unsubstituted heteroaryl groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyamido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, for example, a substituted or unsubstituted cyclopropane, cyclopropene, epoxide, or aziridine ring.

In some embodiments, G is a ring system that contains a 4 membered heterocyclic ring; in some of such embodiments, the heterocyclic ring contains exactly one heteroatom. Independently, in some embodiments, G is a ring system that contains a heterocyclic ring with 5 or more members; in some of such embodiments, the heterocyclic ring contains 1 to 4 heteroatoms. Independently, in some embodiments, the ring in G is unsubstituted; in other embodiments, the ring system contains 1 to 5 substituents; in some of the embodiments in which G contains substituents, each substituent is independently chosen from chemical groups in the category X as defined herein below. Also suitable are embodiments in which G is a carbocyclic ring system.

Among the suitable G groups are, for example, cyclopropyl, cyclobutyl, cyclopent-3-en-1-yl, 3-methoxycyclohexan-1-yl, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, pyridin-2-yl, pyridin-3-yl, pyridin-4-yl, pyrazinyl, pyrimidin-2-yl, pyrimidin-4-yl, pyrimidin-5-yl, pyridazinyl, triazol-1-yl, imidazol-1-yl, thiophen-2-yl, thiophen-3-yl, furan-2-yl, furan-3-yl, pyrrolyl, oxazolyl, isoxazolyl, thiazolyl, isothiazolyl, oxadiazolyl, thiadiazolyl, quinolyl, isoquinolyl, tetrahydrofuryl, pyrrolidinyl, piperidinyl, tetrahydropyranyl, morpholinyl, piperazinyl, dioxolanyl, dioxanyl, indolinyl and 5-methyl-6-chromanyl, adamantyl, norbornyl, and their substituted analogs such as, for example: 3-butyl-pyridin-2-yl, 4-bromo-pyridin-2-yl, 5-carboethoxy-pyridin-2-yl, and 6-methoxyethoxy-pyridin-2-yl.

In some embodiments, each G is independently a substituted or unsubstituted phenyl, pyridyl, cyclohexyl, cyclopentyl, cycloheptyl, pyrolyl, furyl, thiophenyl, triazolyl, pyrazolyl, 1,3-dioxolanyl, or morpholinyl. Among these embodiments include those embodiments, for example, in which G is unsubstituted or substituted phenyl, cyclopentyl, cycloheptyl, or cyclohexyl. In some of these embodiments, G is cyclopentyl, cycloheptyl, cyclohexyl, phenyl, or substituted phenyl. Among embodiments in which G is substituted phenyl are embodiments, for example, in which there are 1, 2, or 3 substituents. Independently, also among embodiments in which G is substituted phenyl are embodiments, for example, in which the substituents are independently selected from methyl, methoxy, and halo.

In some embodiments, one or more cyclopropenes are used in which one or more of $R^1$, $R^2$, $R^3$, and $R^4$ is hydrogen. In some embodiments, $R^1$ or $R^2$ or both $R^1$ and $R^2$ is hydrogen. Independently, in some embodiments, $R^3$ or $R^4$ or both $R^3$ and $R^4$ is hydrogen. In some embodiments, $R^2$, $R^3$, and $R^4$ are hydrogen.

In some embodiments, one or more of $R^1$, $R^2$, $R^3$, and $R^4$ is a structure that has no double bond. Independently, in some embodiments, one or more of $R^1$, $R^2$, $R^3$, and $R^4$ is a structure that has no triple bond. Independently, in some embodiments, one or more of $R^1$, $R^2$, $R^3$, and $R^4$ is a structure that has no halogen atom substituent. Independently, in some embodiments, one or more of $R^1$, $R^2$, $R^3$, and $R^4$ is a structure that has no substituent that is ionic. Independently, in some embodiments, one or more of $R^1$, $R^2$, $R^3$, and $R^4$ is a structure that is not capable of generating oxygen compounds.

In some embodiments of the invention, one or more of $R^1$, $R^2$, $R^3$, and $R^4$ is hydrogen or $(C_1-C_{10})$ alkyl. In some embodiments, each of $R^1$, $R^2$, $R^3$, and $R^4$ is hydrogen or $(C_1-C_8)$ alkyl. In some embodiments, each of $R^1$, $R^2$, $R^3$, and $R^4$ is hydrogen or ($C_1$-$C_4$) alkyl. In some embodiments, each of $R^1$, $R^2$, $R^3$, and $R^4$ is hydrogen or methyl. When $R^1$ is methyl and each of $R^2$, $R^3$, and $R^4$ is hydrogen, the cyclopropene is known herein as "1-MCP."

In some embodiments, a cyclopropene is used that has boiling point at one atmosphere pressure of 50° C. or lower; or 25° C. or lower; or 15° C. or lower. Independently, in some embodiments, a cyclopropene is used that has boiling point at one atmosphere pressure of −100° C. or higher; −50° C. or higher; or −25° C. or higher; or 0° C. or higher.

The cyclopropenes applicable to this invention may be prepared by any method. Some suitable methods of preparation of cyclopropenes are the processes disclosed in U.S. Pat. Nos. 5,518,988 and 6,017,849. Any compound that is not a cyclopropene is known herein as a "non-cyclopropene."

Plants are subject to various biological processes such as, for example, growth, ripening, senescence, maturation, abscission, and degradation. Altering biological processes in plants or plant parts by contacting them with one or more chemical compositions is known as plant growth regulation. Chemical compositions that are effective at causing plant growth regulation are known herein as "plant growth regulators."

Some examples of classes of plant growth regulators that are not cyclopropenes are as follows:

(I) Ethylene, non-cyclopropene ethylene release agents, and non-cyclopropene compounds with high ethylene activity, including, for example, ethepon, abscisic acid, propylene, vinyl chloride, carbon monoxide, acetylene, and 1-butene.

(II) Non-cyclopropene compounds that inhibit ethylene synthesis or ethylene receptor site action or both, including, for example, aminoethoxyvinylglycine and aminooxyacetic acid.

(III) Non-cyclopropene compounds with cytokinin activity, including, for example, benzyl adenine, kinetin, zeatin, adenine, dihydrozeatin, tetrahydropyranylbenzyladenine, dimethylallyladenine, methylthiozeatin, ethoxyethyladenine, benzylaminobenzimidazole, chlorophenylphenylurea, benzthiozolyoxyacetic acid, and fluorophenylbiuret compounds that elicit cytokinin response.

(IV) Non-cyclopropene auxins, including, for example, indoleacetic acid, indolepropionic acid, indolebutyric acid, naphthaleneacetic acid, beta-naphthoxyacetic acid, 4-chlorophenoxyacetic acid, 2,4-dichlorooxyacetic acid, trichlorophenoxyacetic acid, trichloro benzoic acid, and 4 amino 3,5,6 trichloropicolinic acid.

(V) Gibberellins, including, for example, $GA_2$, $GA_3$, $GA_4$, $GA_5$, $GA_7$, and $GA_8$ having variously substituted giberellin backbone structures, helminthosporic acid, phaseolic acid, kaurenoic acid, and steviol.

(VI) Cofactors and inhibitors of IAA oxidase, including, for example, chlorogenic acid, coumaric acid, quercitin, and caffeic acid.

(VII) Non-cyclopropene secondary growth inhibitors, including, for example, methyl jasmonate.

(VIII) Non-cyclopropene natural growth hormones, including, for example, natural growth hormones derived from, for example, kelp, algae, and bacteria.

In some embodiments, the practice of the present invention involves the use of at least one plant growth regulator that is not a cyclopropene. Independently, some embodiments are contemplated that are performed without using any member of one of the classes of plant growth regulators that are not cyclopropenes; such embodiments may or may not use one or more members of the remaining classes of plant growth regulators that are not cyclopropenes. For example, embodiments are envisioned that do not use any member of class I (defined herein above), but such embodiments may or may not use one or member of any of classes II-VIII. Independently, in some embodiments, the practice of the present invention is performed without the use of any compound that is a plant growth regulator that is not a cyclopropene.

In some embodiments, one or more composition of the present invention includes at least one fungicidally active compound. Independently, in some embodiments, the composition of the present invention does not include aminoethyl vinylglycine. Independently, in some embodiments, the composition of the present invention does not include any derivatives of vinylglycine.

Independently, in some embodiments, the composition of the present invention does not include any compound that is a strobilurin. Strobilurins are known in the art and are defined, for example, by Harden, et. al., in WO 2005/044002. Independently, in some embodiments, the composition of the present invention does not include any compound that is not a cyclopropene and that is a fungicidally active compound.

In some embodiments, one or more composition of the present invention includes at least one ionic complexing reagent. An ionic complexing reagent interacts with a cyclopropene to form a complex that is stable in water. Some suitable ionic complexing reagents, for example, include lithium ion. In some embodiments, no ionic complexing reagent is used.

In some embodiments, no composition of the present invention includes any molecular encapsulating agent. In other embodiments, one or more composition of the present invention includes at least one molecular encapsulating agent.

When a molecular encapsulating agent is used, suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is alpha-cyclodextrin, beta-cyclodextrin, gamma-cyclodextrin, or a mixture thereof. In some embodiments of the invention, particularly when the cyclopropene is 1-methylcyclopropene, the encapsulating agent is alpha-cyclodextrin. The preferred encapsulating agent will vary depending upon the structure of the cyclopropene or cyclopropenes being used. Any cyclodextrin or mixture of cyclodextrins, cyclodextrin polymers, modified cyclodextrins, or mixtures thereof can also be utilized pursuant to the present invention. Some cyclodextrins are available, for example, from Wacker Biochem Inc., Adrian, Mich. or Cerestar USA, Hammond, Ind., as well as other vendors.

In some of the embodiments in which a molecular encapsulating agent is present, at least one molecular encapsulating agent encapsulates one or more cyclopropenes. A cyclopropene or substituted cyclopropene molecule encapsulated in a molecule of a molecular encapsulating agent is known herein as a "cyclopropene molecular encapsulating agent complex." The cyclopropene molecular encapsulation agent complexes can be prepared by any means. In one method of preparation, for example, such complexes are prepared by contacting the cyclopropene with a solution or slurry of the molecular encapsulation agent and then isolating the complex, using, for example, processes disclosed in U.S. Pat. No. 6,017,849. For example, in one method of making a complex in which 1-MCP is encapsulated in a molecular encapsulating agent, the 1-MCP gas is bubbled through a solution of alpha-cyclodextrin in water, from which the complex first precipitates and is then isolated by filtration. In some embodiments, complexes are made by the above method and, after isolation, are dried and stored in solid form, for example as a powder, for later addition to useful compositions.

In some embodiments, one or more molecular encapsulating agent and one or more cyclopropenes are both present in a composition; in some of such embodiments, the amount of molecular encapsulating agent can usefully be characterized by the ratio of moles of molecular encapsulating agent to moles of cyclopropene. In some embodiments, the ratio of moles of molecular encapsulating agent to moles of cyclopropene is 0.1 or larger; or 0.2 or larger; or 0.5 or larger; or 0.9 or larger. Independently, in some of such embodiments, the ratio of moles of molecular encapsulating agent to moles of cyclopropene is 2 or lower; or 1.5 or lower.

In some embodiments, the composition of the present invention has no abscission agent.

In the practice of the present invention, the composition may be contacted with a plant in a variety of ways. For example, the composition of the present invention may be a solid, a liquid, a gas, or a mixture thereof.

In some embodiments, a plant is contacted with at least one composition of the present invention that is a gas. Among such embodiments, it is contemplated that the plant being treated will be surrounded by a normal ambient atmosphere (at approximately 1 atmosphere pressure) to which composition of the present invention has been added. In some embodiments, the concentration of cyclopropene is 0.1 nl/l (i.e., nanoliter per liter) or higher; or 1 nl/l or higher, or 10 nl/l or higher; or 100 nl/l or higher. Independently, in some embodiments, the concentration of cyclopropene is 3,000 nl/l or lower; or 1,000 nl/l or lower.

In some embodiments, the practice of the present invention involves one or more liquid compositions. In some embodiments, liquid compositions are liquid at 25° C. In some embodiments, liquid compositions are liquid at the temperature at which the composition is used to treat plants. Because plants are often treated outside of any buildings, plants may be treated at temperatures ranging from 1° C. to 45° C.; suitable liquid compositions need not be liquid over that entire range, but suitable liquid compositions are liquid at some temperature from 1° C. to 45° C.

A liquid composition of the present invention may be a single pure substance, or it may contain more than one substance. If a liquid composition contains more than one substance, that liquid composition may be a solution or a dispersion or a combination thereof. If, in the liquid composition, one substance is dispersed in another substance in the form of a dispersion, the dispersion may be of any type, including, for example, a suspension, a latex, an emulsion, a miniemulsion, a microemulsion, or any combination thereof.

Among embodiments in which the composition of the present invention is a liquid, the amount of cyclopropene in the composition may vary widely, depending on the type of composition and the intended method of use. In some embodiments, the amount of cyclopropene, based on the total weight of the composition, is 4% by weight or less; or 1% by weight or less; or 0.5% by weight or less; or 0.05% by weight or less. Independently, in some embodiments, the amount of cyclopropene, based on the total weight of the composition, is 0.000001% by weight or more; or 0.00001% by weight or more; or 0.0001% by weight or more; or 0.001% by weight or more.

Among embodiments of the present invention that use a composition of the present invention that contains water, the amount of cyclopropene may be characterized as parts per million (i.e., parts by weight of cyclopropene per 1,000,000 parts by weight of water in the composition, "ppm") or as parts per billion (i.e., parts by weight of cyclopropene per 1,000,000,000 parts by weight of water in the composition, "ppb"). In some embodiments, the amount of cyclopropene is 1 ppb or more; or 10 ppb or more; or 100 ppb or more. Independently, in some embodiments, the amount of cyclopropene is 10,000 ppm or less; or 1,000 ppm or less.

In some embodiments, a composition of the present invention that is a liquid is used in which some or all of the cyclopropene is encapsulated in one or more encapsulating agent In some embodiments, no composition of the present invention includes one or more metal-complexing agents. In some embodiments, one or more compositions of the present invention includes one or more metal-complexing agents.

Among embodiments in which one or more liquid compositions are used, in some of such embodiments, one or more metal-complexing agents may be included in one or more liquid compositions. A metal-complexing agent is a compound that is capable of forming coordinate bonds with metal atoms. Some metal-complexing agents are chelating agents. As used herein, a "chelating agent" is a compound, each molecule of which is capable of forming two or more coordinate bonds with a single metal atom. Some metal-complexing agents form coordinate bonds with metal atoms because the metal-complexing agents contain electron-donor atoms that participate in coordinate bonds with metal atoms. Suitable chelating agents include, for example, organic and inorganic chelating agents. Among the suitable inorganic chelating agents are, for example, phosphates such as, for example, tetrasodium pyrophosphate, sodium tripolyphosphate, and hexametaphosphoric acid. Among the suitable organic chelating agents are those with macrocyclic structures and non-macrocyclic structures. Among the suitable macrocyclic organic chelating agents are, for example, porphine compounds, cyclic polyethers (also called crown ethers), and macrocyclic compounds with both nitrogen and oxygen atoms.

Some suitable organic chelating agents that have non-macrocyclic structures are, for example, aminocarboxylic acids, 1,3-diketones, hydroxycarboxylic acids, polyamines, aminoalcohols, aromatic heterocyclic bases, phenol, aminophenols, oximes, Shiff bases, sulfur compounds, and mixtures thereof. In some embodiments, the chelating agent includes one or more aminocarboxylic acids, one or more hydroxycarboxylic acids, one or more oximes, or a mixture thereof. Some suitable aminocarboxylic acids include, for example, ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis(hydroxyphenylglycine) (EHPG), and mixtures thereof. Some suitable hydroxycarboxylic acids include, for example, tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, EDTA is used.

Some additional suitable chelating agents are polymeric. Some suitable polymeric chelating agents include, for example, polyethyleneimines, polymethacryloylacetones, poly(acrylic acid), and poly(methacrylic acid). Poly(acrylic acid) is used in some embodiments.

Some suitable metal-complexing agents that are not chelating agents are, for example, alkaline carbonates, such as, for example, sodium carbonate.

Metal-complexing agents may be present in neutral form or in the form of one or more salts. Mixtures of suitable metal-complexing agents are also suitable.

In some embodiments of the present invention, no composition contains water.

In some embodiments, the composition of the present invention contains water; in some of such embodiments, the water contains one or more metal ions, such as, for example, iron ions, copper ions, other metal ions, or mixtures thereof. In some embodiments, the water contains 0.1 ppm or more of one or more metal ions.

Among embodiments that use one or more metal-complexing agents, the amount of metal-complexing agent used may vary widely. In some embodiments in which at least one liquid composition is used, the amount of metal-complexing agent in that liquid composition will be adjusted to be sufficient to complex the amount of metal ion that is present or expected to be present in the liquid composition that contains the metal-complexing agent. For example, in some embodiments in which a liquid composition of the present invention is used that includes water that contains some metal ion, if a relatively efficient metal-complexing agent is used (i.e., a metal-complexing agent that will form a complex with all or nearly all the metal ions in the water), the ratio of moles of metal-complexing agent to moles of metal ion will be 0.1 or greater; or 0.2 or greater; or 0.5 or greater; or 0.8 or greater. Among such embodiments that use a relatively efficient metal-complexing agent, the ratio of moles of metal-complexing agent to moles of metal ion will be 2 or less; or 1.5 or less; or 1.1 or less. It is contemplated that, if a less-efficient metal-complexing agent is used, the ratio of moles of metal-complexing agent to moles of metal ion could be increased to compensate for the lower efficiency.

Independently, in some embodiments in which a liquid composition is used, the amount of metal-complexing agent is, based on the total weight of the liquid composition, 25% by weight or less; or 10% by weight or less; or 1% by weight or less. Independently, in some embodiments, the amount of metal-complexing agent is, based on the total weight of the liquid composition, 0.00001% or more; or 0.0001% or more; or 0.01% or more.

Independently, in some embodiments in which a liquid composition that includes water is used, the amount of metal-complexing agent can usefully be characterized by the molar concentration of metal-complexing agent in the water (i.e., moles of metal-complexing agent per liter of water). In some of such liquid compositions, the concentration of metal-complexing agent is 0.00001 mM (i.e., milli-Molar) or greater; or 0.0001 mM or greater; or 0.001 mM or greater; or 0.01 mM or greater; or 0.1 mM or greater. Independently, in some embodiments in which a liquid composition of the present invention includes water, the concentration of metal-complexing agent is 100 mM or less; or 10 mM or less; or 1 mM or less.

In some embodiments of the present invention, one or more adjuvants is also included in the composition of the present invention. The use of adjuvants is considered optional in the practice of the present invention. Adjuvants may be used alone or in any combination. When more than one adjuvant is used, it is contemplated that any combination of one or more adjuvants may be used. Some suitable adjuvants are surfactants, alcohols, oils, extenders, pigments, fillers, binders, plasticizers, lubricants, wetting agents, spreading agents, dispersing agents, stickers, adhesives, defoamers, thickeners, transport agents, and emulsifying agents.

In some embodiments, a composition of the present invention is used that contains at least one adjuvant selected from alcohols, oils, and mixtures thereof; such a composition may or may not additionally contain one or more surfactant.

Among embodiments in which one or more liquid compositions are used, various embodiments are contemplated that include the use of, for example, any one or more of the following liquid compositions: liquid compositions that contain one or more surfactant but no oil and no alcohol; liquid compositions that contain one or more oil but no surfactant and no alcohol; and liquid compositions that contain one or more alcohol but no surfactant and no oil. In some embodiments, one or more liquid compositions are used that each contain one or more surfactant and one or more oil; or one or more liquid compositions are used that each contain one or more surfactant and one or more alcohol. In some embodiments, one or more liquid compositions are used that each contain one or more surfactant, one or more oil, and one or more alcohol.

In some embodiments, at least one liquid composition is used that contains no organosilicate compound. In some embodiments, no organosilicate compound is used.

In some embodiments of the present invention, one or more surfactants are used. Suitable surfactants include, for example, anionic surfactants, cationic surfactants, nonionic surfactants, amphoteric surfactants, and mixtures thereof.

One group of suitable anionic surfactants are the sulfosuccinates, including, for example, alkaline salts of mono- and dialkyl sulfosuccinates. In some embodiments, sodium salts of dialkyl sulfosuccinates are used, including, for example, those with alkyl groups with 4 carbons or more, or 6 carbons or more. In some embodiments, sodium salts of dialkyl sulfosuccinates are used, including, for example, those with alkyl groups with 18 carbons or fewer; or 14 carbons or fewer; or 10 carbons or fewer. One suitable sodium salt of a dialkyl sulfosuccinate is, for example, sodium di-hexyl sulfosuccinate. One other suitable sodium salt of a dialkyl sulfosuccinate is, for example, sodium di-octyl sulfosuccinate.

Another group of suitable anionic surfactants are the sulfates and sulfonates, including, for example, alkaline salts of alkyl sulfates. In some embodiments, sodium salts of alkyl sulfates are used, including, for example, those with alkyl groups with 4 carbons or more, or 6 carbons or more, or 8 carbons or more. In some embodiments, sodium salts of alkyl sulfates are used, including, for example, those with alkyl groups with 18 carbons or fewer; or 14 carbons or fewer; or 10 carbons or fewer. One suitable sodium salt of an alkyl sulfate is, for example, sodium dodecyl sulfate.

Some suitable surfactants are, for example, sodium di-octyl sulfosuccinate, sodium di-hexyl sulfosuccinate, sodium dodecyl sulfate, polyglycerol esters, alcohol ethoxylates, alkylphenol ethoxylates (such as, for example, Triton™ X-100 from Dow), cetyl pyridinium bromide, ethoxylated alkyl amines, alcohol amines (such as, for example, ethanolamines), saponins, and silicone-based surfactants (such as, for example, Silwet™ L-77 surfactant from OSi Specialties).

Mixtures of suitable surfactants are also suitable.

Suitable surfactants have various properties. For example, some are excellent at enabling cyclopropene to remain in contact with certain plants or plant parts; some are readily soluble in the other ingredients of the formulation; some do not cause phytotoxicity in plants or plant parts. Very few surfactants excel in every property, but, when one or more surfactants are used, the practitioner will readily be able to choose a surfactant or mixture of surfactants with the balance of properties most appropriate for the desired use, taking into account, for example, the species desired to be treated and the other ingredients intended to be used in the composition.

Among embodiments in which one or more liquid compositions are used that include one or more surfactants, some liquid compositions contain surfactant in amounts, by weight based on the total weight of the liquid composition, of 0.025% or more; or 0.05% or more; or 0.1% or more. Independently, some liquid compositions use surfactant in amounts, by weight based on the total weight of the liquid composition, of 75% or less; or 50% or less; or 20% or less; or 5% or less; or 2% or less; 1% or less; or 0.5% or less; or 0.3% or less.

In some of the embodiments in which a liquid composition is used, no oil is included in the composition.

Independently, in some of the embodiments in which a liquid composition is used, one or more oils are used. As used herein, an "oil" is a compound that is liquid at 25° C. and 1 atmosphere pressure and that has a boiling point at 1 atmosphere pressure of 30° C. or higher. As used herein, "oil" does not include water, does not include surfactants (as described herein above), and does not include alcohols (as described herein below). Some oils are hydrocarbon oils, while other oils are non-hydrocarbon oils. Hydrocarbon oils are straight, branched, or cyclic alkane compounds with 6 or more carbon atoms. As used herein, "non-hydrocarbon" means any compound that contains at least one atom that is neither hydrogen nor carbon.

In some embodiments in which a liquid composition is used, one or more hydrocarbon oils are included in the composition. In some embodiments, hydrocarbon oils are obtained from petroleum distillation and contain a mixture of alkane compounds, along with, in some cases, impurities. In some embodiments, hydrocarbon oils are used that contain 18 or fewer carbon atoms. Some suitable hydrocarbon oils include, for example, hexane, decane, dodecane, hexadecane, diesel oil, refined paraffinic oil (e.g., Ultrafine™ spray oil from Sun Company), and mixtures thereof.

In some embodiments in which a liquid composition is used, one or more non-hydrocarbon oils are included in the composition. In some embodiments, non-hydrocarbon oils have boiling point of 50° C. or higher; or 75° C. or higher; or 100° C. or higher. Independently, in some embodiments, non-hydrocarbon oils have molecular weight of 100 or higher; or 200 or higher; or 500 or higher.

Some suitable non-hydrocarbon oils are, for example, fatty non-hydrocarbon oils. "Fatty" means herein any compound that contains one or more residues of fatty acids. Fatty acids are long-chain carboxylic acids, with chain length of at least 4 carbon atoms. Typical fatty acids have chain length of 4 to 18 carbon atoms, though some have longer chains. Linear, branched, or cyclic aliphatic groups may be attached to the long chain. Fatty acid residues may be saturated or unsaturated, and they may contain functional groups, including for example alkyl groups, epoxide groups, halogens, sulfonate groups, or hydroxyl groups, that are either naturally occurring or that have been added. Some suitable fatty non-hydrocarbon oils are, for example, fatty acids; esters of fatty acids; amides of fatty acids; dimers, trimers, oligomers, or polymers thereof; and mixtures thereof.

Some of the suitable fatty non-hydrocarbon oils, are, for example, esters of fatty acids. Such esters include, for example, glycerides of fatty acids. Glycerides are esters of fatty acids with glycerol, and they may be mono-, di-, or triglycerides. A variety of triglycerides are found in nature. Most of the naturally occurring triglycerides contain residues of fatty acids of several different lengths and/or compositions. Some suitable triglycerides are found in animal sources such as, for example, dairy products, animal fats, and fish. Further examples of suitable triglycerides are oils found in plants, such as, for example, coconut, palm, cottonseed, olive, tall, peanut, safflower, sunflower, corn, soybean, linseed, tung, castor, canola, *citrus* seed, cocoa, oat, palm, palm kernel, rice bran, cuphea, or rapeseed oil.

Among the suitable triglycerides, independent of where they are found or how they are made, are those, for example, that contain at least one fatty acid residue that has 14 or more carbon atoms. Some suitable triglycerides have fatty acid residues that contain 50% or more by weight, based on the weight of the residues, fatty acid residues with 14 or more carbon atoms, or 16 or more carbon atoms, or 18 or more carbon atoms. One example of a suitable triglyceride is soybean oil.

Suitable fatty non-hydrocarbon oils may be synthetic or natural or modifications of natural oils or a combination or mixture thereof. Among suitable modifications of natural oils are, for example, alkylation, hydrogenation, hydroxylation, alkyl hydroxylation, alcoholysis, hydrolysis, epoxidation, halogenation, sulfonation, oxidation, polymerization, and combinations thereof. In some embodiments, alkylated (including, for example, methylated and ethylated) oils are used. One suitable modified natural oil is methylated soybean oil.

Also among the suitable fatty non-hydrocarbon oils are self-emulsifying esters of fatty acids.

Another group of suitable non-hydrocarbon oils are silicone oils Silicone oils are oligomers or polymers that have a backbone that is partially or fully made up of —Si—O— links. Silicone oils include, for example, polydimethylsiloxane oils. Polydimethylsiloxane oils are oligomers or polymers that contain units of the form

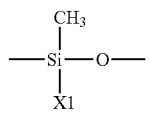

where at least one of the units has $X1=CH_3$. In other units, X1 may be any other group capable of attaching to Si, including, for example, hydrogen, hydroxyl, alkyl, alkoxy, hydroxyalkyl, hydroxyalkoxy, alkylpolyalkoxyl, substituted versions thereof, or combinations thereof. Substituents may include, for example, hydroxyl, alkoxyl, polyethoxyl, ether linkages, ester linkages, amide linkages, other substitutents, or any combination thereof. In some suitable polydimethylsiloxane oils, all X1 groups are methyl. In some suitable polydimethylsiloxanes, at least one unit has an X1 group that is not methyl; if more than one non-methyl X1 unit is present, the non-methyl X1 units may be the same as each other, or two or more different non-methyl X1 units may be present. Polydimethylsiloxane oils may be end-capped with any of a wide variety of chemical groups, including, for example, hydrogen, methyl, other alkyl, or any combination thereof. Also contemplated are cyclic polydimethylsiloxane oils.

Mixtures of suitable oils are also suitable, including mixtures of plural hydrocarbon oils, mixtures of plural non-hydrocarbon oils, and mixtures of one or more hydrocarbon oil with one or more non-hydrocarbon oil.

Some embodiments use oil in amounts, by weight based on the total weight of the composition, of 0.25% or more; or 0.5% or more; or 1% or more. Independently, some embodiments use oil in amounts, by weight based on the total weight of the composition, of 90% or less; or 50% or less; or 10% or less; or 5% or less; or 4% or less; or 3% or less.

Among embodiments in which one or more liquid compositions are used, in some liquid compositions, one or more alcohols are used. Suitable alcohols include, for example, alkyl alcohols and other alcohols. As used herein, alkyl alcohols are alkyl compounds with one hydroxyl group; the alkyl group may be linear, branched, cyclic, or a combination thereof; the alcohol may be primary, secondary, or tertiary. In some embodiments, alkyl alcohols are used which have alkyl groups with 2 or more carbon atoms. In some embodiments, ethanol, isopropanol, or a mixture thereof is used. In some embodiments, one or more alkyl alcohols are used which have alkyl groups with 20 or fewer carbon atoms; or 10 or fewer carbon atoms; or 6 or fewer carbon atoms; or 3 or fewer carbon atoms.

Among liquid compositions that use alcohol, some liquid compositions use alcohol in amounts, by weight based on the total weight of the liquid composition, of 0.25% or higher; or 0.5% or higher, or 1% or higher. Among liquid compositions that use alcohol, some liquid compositions use alcohol in amounts, by weight based on the total weight of the liquid composition, of 90% or less; or 50% or less; or 10% or less; or 5% or less; or 4% or less; or 3% or less.

The ingredients of the present invention may be admixed by any means, in any order.

In the practice of the present invention, any method may be used that allows the composition or compositions of the present invention to contact the plant. Among embodiments in which one or more liquid compositions are used, some examples of methods of contact are, for example, spraying, foaming, fogging, pouring, brushing, dipping, similar methods, and combinations thereof. In some embodiments, spraying or dipping or both is used. In some embodiments, spraying is used.

Among embodiments in which a composition of the present invention is sprayed, any spray conditions may be used. For example, nozzle size and pressure may be chosen by the practitioner of the present invention to achieve desired results. Some useful nozzle types are, for example, flat fan, pre-orifice flat fan, hollow cone, full cone, air inclusion, low drift, and flooding. Independently, some useful spray pressures are, for example, 127 kPa (15 psi), 422 kPa (50 psi), 844 kPa (100 psi), 1689 kPa (200 psi), and 2534 kPa (300 psi). Spray pressures that are intermediate between any pair of these useful spray pressures are, in some embodiments, also useful. Independently, in some embodiments, the spray conditions are chosen to achieve certain droplet size; some useful droplet sizes are, for example, 50 micrometers, 100 micrometers, 200 micrometers, 300 micrometers, 400 micrometers, 600 micrometers, and 800 micrometers. Droplet sizes that are intermediate between any pair of these useful droplet sizes are, in some embodiments, also useful.

After a plant is contacted with one or more compositions of the present invention, any ingredients that interact with the plant may begin that interaction right away, or such ingredients, independently of each other, may interact with the plant at a later time. For example, the liquid composition may form a release coating on all or part of the plant, and one or more ingredients may become available, over time, to interact with the plant.

A composition of the present invention is used to contact plants. It is contemplated that, in performing the treatment, the composition of the present invention may be contacted with the entire plant or may be contacted with one or more plant parts. Plant parts include any part of a plant, including, for example, flowers, buds, blooms, seeds, cuttings, roots, bulbs, fruits, vegetables, leaves, and combinations thereof.

In some embodiments, the composition of the present invention is a liquid, and the liquid is sprayed onto crop plants growing in a field. Such a spraying operation may be performed one time or more than one time on a particular group of crop plants during a single growing season. In some embodiments, the amount of cyclopropene used in one spraying operation is 0.1 gram per hectare (g/ha) or more; or 0.5 g/ha or more; or 1 g/ha or more; or 5 g/ha or more; or 25 g/ha or more; or 50 g/ha or more; or 100 g/ha or more. Independently, in some embodiments, the amount of cyclopropene used in one spraying operation is 6000 g/ha or less; or 3000 g/ha or less; or 1500 g/ha or less.

Some plants are grown for the purpose of removing one or more plant parts, when such parts are considered a useful product. Such plants are known herein as "crop plants." Removal of such useful plant parts is known as harvesting. In the practice of the present invention, plants that produce useful plant parts are treated with composition of the present invention prior to the harvesting of the useful plant parts. In such embodiments, each composition that is used may, independently of any other compositions that may be used, be brought into contact with all of or with some portion of the plant. If a composition is brought into contact with a portion of the plant, that portion may or may not include the useful plant part intended to be harvested.

In the practice of the present invention, at least one treatment is performed on crop plants before any useful plant parts are harvested. The growth and development process of many crop plants can be described by certain developmental stages. For example, many crop plants develop through vegetative stages followed by reproductive stages. In some embodiments, crop plants are contacted with a composition of the present invention one or more times during one or more vegetative stages. Independently, in some embodiments, crop plants are contacted with a composition of the present invention one or more times during one or more reproductive stages. Also contemplated are embodiments in which crop plants are contacted with a composition of the present invention one or more times during one or more vegetative stages and also contacted with a composition of the present invention one or more times during one or more reproductive stages. Some crop plants develop through ripening stages after their reproductive stages; it is contemplated in some embodiments to contact such crop plants with one or more composition of the present invention one or more times during one or more ripening stage, either in addition to or instead of contact with one or more composition of the present invention during other stage or stages.

Some crop plants develop through vegetative and reproductive processes simultaneously. It is contemplated to contact such crop plants with one or more composition of the present invention one or more times after germination but before harvest.

It is contemplated that, for some specific crop plants, there may be an optimum stage or stages at which to perform the contact with the composition of the present invention, in order to achieve the maximum improvement in crop yield. It is contemplated that such optimum stage or stages may be different for each type of crop plant, and such optimum stage or stages may, in some cases, depend on the specific growing conditions.

In some embodiments, it is contemplated to contact a group of crop plants at a certain desired stage of development. In such cases, it is contemplated that such contacting may be performed when the ratio of the number of plants that have reached the desired stage of development to the total number of plants in the group is at least 0.1, or at least 0.5, or at least 0.75, or at least 0.9 (i.e., when the portion of plants that have reached the desired stage of development is at least 10%, or 50%, or 75%, or 90%).

For example, soybean plants develop through vegetative stages followed by reproductive stages. Some of the vegetative stages are VE (emergence), VC (cotyledon), V1 (fully developed leaves at unifoliate node), and VN ("N" is the number of nodes on the main stem that have fully developed leaves). Some of the reproductive stages are R1 (beginning bloom), R2 (full bloom), R3 (beginning pod), R4 (full pod), R5 (beginning seed), R5.5 (intermediate between R5 and R6), R6 (full seed), R7 (beginning maturity), and R8 (full maturity). In some embodiments, soybean plants are contacted with a composition of the present invention one or more times during one or more of any vegetative stage, one or more of any reproductive stage, or any combination thereof. In some embodiments, soybean plants are contacted with a composition of the present invention during one or more of V3, V4, V5, or V6 and, optionally, also one or more times during one or more reproductive stage. In some embodiments, soybean plants are contacted with a composition of the present invention one or more times during R1, R2, R3, R5, or R5.5. Also contemplated are embodiments, for example, in which soybean plants are contacted with one or more compositions of the present invention during plural stages, for example, during R2 and R3; during R2 and R5.5, during R3 and R5.5; or during R2, R3, and R5.5. Independently, in some embodiments, soybean plants are contacted with one or more composition of the present invention one or more times during or after stage V3 and, optionally, at one or more later stages. Independently, in some embodiments, soybean plants are contacted with one or more composition of the present invention one or more times during or after stage R1 and, optionally, at one or more later stages. Independently, some embodiments involve spraying soybean plants with at least one liquid composition comprising at least one cyclopropene, after at least 10% of said soybean plants have at least one node on the main stem with at least one fully developed leaf. Some embodiments involve spraying soybean plants with at least one liquid composition comprising at least one cyclopropene, after at least 10% of said soybean plants have begun to bloom.

As another example, corn plants also develop through vegetative stages followed by reproductive stages. The vegetative growth stages of corn plants include VE (emergence), V1 (emergence of first leaf), VN (emergence of Nth leaf), VNMAX (emergence of last leaf), and VT (tasselling). One of these vegetative stages is V5, which begins when the fifth leaf emerges. Another of these vegetative stages is V12, which begins when the twelfth leaf emerges. The reproductive growth stages of corn plants include R1 (silking), R2 (blister), R3 (milk), R4 (dough), R5 (dent), R6 (maturity). In some embodiments, corn plants are contacted with one or more composition of the present invention during or after any of V5 (emergence of fifth leaf), V12 (emergence of 12th leaf), VT, R3, or during or after any combination of two or more of V6, V12, VT, and R3. Independently, in some embodiments, corn plants are contacted with one or more composition of the present invention during V12, during VT, and during R3. Independently, some embodiments involve spraying corn plants one or more times with at least one liquid composition comprising at least one cyclopropene, after at least 10% of said corn plants have reached the developmental stage at which the fifth leaf is fully expanded, or after at least 10% of said corn plants have reached the developmental stage at which the twelfth leaf is fully expanded.

As another example, cotton plants are believed to simultaneously produce vegetative and fruiting structures. However, cotton plants develop through well-known stages. One such stage is the emergence of seedlings. A subsequent stage is marked by the appearance of pinhead squares. In some embodiments, cotton plants are contacted one or more times with one or more composition of the present invention after seedling emergence. In some embodiments, cotton plants are contacted one or more times with one or more composition of the present invention soon (i.e., three days or less) after the appearance of pinhead squares. In some embodiments, cotton plants are contacted with one or more composition of the present invention soon after the appearance of pinhead squares and are then subsequently contacted with one or more composition of the present invention at one or more later time (i.e., 7 days or more after the previous treatment).

Independently, some embodiments involve spraying cotton plants one or more times with at least one liquid composition comprising at least one cyclopropene, after at least 10% of said cotton plants have developed pinhead squares.

A further example is rice plants. In the practice of the present invention, rice plants may be contacted one or more times with one or more composition of the present invention during one or more vegetative stage, one or more reproductive stage, one or more ripening stage, or any combination thereof.

An additional example is wheat plants, which grow through developmental stages that are commonly described with the well-known Feekes scale. In the practice of the present invention, wheat plants may be contacted one or more times with one or more composition of the present invention during one or more stages on the Feekes scale, or during any combination thereof. Some of the stages on the Feekes scale are, for example, F8.0 (flag leaf visible), F9.0 (ligule of flag leaf visible), F10.0 (boot stage), and F10.5 (heading complete). In some embodiments, wheat plants are contacted with one or more composition of the present invention during or after any one or more of F8.0, F9.0, F10.0, or F10.5. In some embodiments, wheat plants are contacted with one or more composition of the present invention during two or more of F8.0, F9.0, F10.0, and F10.5. In some embodiments, wheat plants are contacted with one or more composition of the present invention during each of F8.0, F9.0, F10.0, and F10.5. Independently, in some embodiments, wheat plants are contacted with one or more composition of the present invention at least once after at least 10% of the wheat plants have reached F9.0 growth stage. Independently, some embodiments involve spraying wheat plants one or more times with at least one liquid composition comprising at least one cyclopropene, after at least 10% of the wheat plants have reached the developmental stage at which the flag leaf is visible.

In some embodiments, wheat plants are treated that are selected from one or more varieties that do not include either or both of the varieties Halberd and Karl92. In some embodiments, the plants that are treated do not include wheat.

Yet another example is oilseed rape plants, also called rapeseed plants. In some embodiments, oilseed rape plants are contacted with at least one composition of the present invention after at least 10% of the oilseed rape plants have begun to bloom Suitable treatments may be performed on plants that are planted in a field, in a garden, in a building (such as, for example, a greenhouse), or in another location. Suitable treatments may be performed on a plants that are planted in open ground, in one or more containers (such as, for example, a pot, planter, or vase), in confined or raised beds, or in other places.

In some embodiments, treatment is performed on plants that are in a location other than in a building.

In some embodiments, plants are treated while they are growing in a container such as, for example, pots, flats, or portable beds. In some of such cases, when treated plants are subsequently transplanted to open ground, the treated plants resist the stress of transplantation better than untreated plants do. In some embodiments, such resistance to transplantation stress can lead to improved crop yield. For example, tomatoes that are treated according to the practice of the present invention and that are transplanted can sometimes show improved resistance to transplantation stress and, sometimes, improved crop yield, in comparison to untreated tomato plants.

In the practice of the present invention, the plants that are treated may be any plants that produce a useful product. Normally, a specific part of the plant forms the useful product. A plurality of useful plant parts, after removal from a plurality of plants, is known as a "crop." Some types of plants have a single type of useful plant part, while other types of plants have plural types of useful plant parts.

Among the plants that are suitable for use in the present invention, are, for example, those with plant parts that are edible, those with plant parts that are non-edible but useful for some other purpose, and combinations thereof. Also contemplated as suitable plants are those from which useful materials can be extracted; such useful materials may be, for example, edible materials, raw materials for manufacturing, medicinally useful materials, and materials useful for other purposes.

Further contemplated as suitable plants are those that yield plant parts that are useful for their beauty and/or ornamental properties. Such ornamental plant parts include, for example, flowers and other ornamental plant parts such as, for example, ornamental leaves. Some of such plants produce useful bulbs. In some embodiments, an entire ornamental plant is considered to be the useful plant part.

Also suitable are plants that produce edible plant parts. Plants that produce all types of edible plant parts are contemplated as suitable for use in the present invention.

Many of the plants that are suitable for use in the practice of the present invention can be usefully divided into categories or groups. One useful method for defining such groups is the "Definition and Classification of Commodities," published on or before Mar. 23, 2006, by the Food and Agriculture Organization ("FAO") of the United Nations as a "Draft."

In the practice of some embodiments of the present invention, it is contemplated to use plants that produce one or more crops that fall within any one of the following crop groups.

Also contemplated are embodiments in which plants that produce two or more crops are used. In such embodiments, a single plant type that produces two or more crops may be used, or a mixture of two or more plants that produce different crops from each other may be used, or any combination thereof. Independently, if two or more crops are used, they may be from the same crop group or from different crop groups.

Crop Group 1 is cereals, including, for example, wheat, rice, barley, corn, popcorn, rye, oats, millet, sorghum, buckwheat, quiona, fonio, triticale, canary seed, canagua, quihuicha, adlay, wild rice, and other cereals. In some embodiments of the present invention, suitable plants are those that produce wheat or rice or corn or sorghum. In some embodiments, corn plants are suitable. In some embodiments, wheat plants are suitable.

Crop Group 2 roots and tubers, including, for example, potatoes, sweet potatoes, cassava, yautia (cocomay), taro (cocoyam), yams, and other roots and tubers. Also considered herein as a suitable root crop is chinese water chestnut (*Eleocharis dulcis*).

Crop Group 3 is sugar crops, including, for example, sugar cane, sugar beet, sugar maple, sweet sorghum, sugar palm, and other sugar crops.

Crop Group 4 is pulses, including, for example, beans (including, for example, kidney, haricot, lima, butter, adzuki, mungo, golden, green gram, black gram, urd, scarlet runner, rice, moth, tepary, lablab, hyacinth, jack, winged, guar, velvet, yam, and other beans), horse-bean, broad bean, field bean, garden pea, chickpea, bengal gram, garbanzo, cowpea, blackeyed pea, pigeon pea, cajan pea, congo bean, lentil, bambara ground nut, earth pea, vetches, lupins, and other pulses.

Crop Group 5 is nuts, including, for example, brazil nuts, cashew nuts, chestnuts, almonds, walnuts, pistachios, kola nuts, hazelnuts, areca nuts, pecan nut, butter nut, pili nut, Java almond, paradise nut, macadamia nut, pignolia nut, and other nuts.

Crop Group 6 is oil-bearing crops, including, for example, soybeans, groundnuts (including peanuts), coconuts, oil palm fruit, olives, karite nuts, castor beans, sunflower seeds, rapeseed, canola, tung nuts, safflower seed, sesame seed, mustard seed, poppy seed, melonseed, tallowtree seeds, kapok fruit, seed cotton, linseed, hempseed, and other oilseeds. In some embodiments, soybean plants are suitable.

Crop Group 7 is vegetables, including, for example, cabbages, artichokes, asparagus, lettuce, spinach, cassava leaves, tomatoes, cauliflower, pumpkins, cucumbers and gherkins, eggplants, chilies and peppers, green onions, dry onions, garlic, leek, other alliaceous vegetables, green beans, green peas, green broad beans, string beans, carrots, okra, green corn, mushrooms, watermelons, cantaloupe melons, bamboo shoots, beets, chards, capers, cardoons, celery, chervil, cress, fennel, horseradish, marjoram, oyster plant, parsley, parsnips, radish, rhubarb, rutabaga, savory, scorzonera, sorrel, watercress, and other vegetables.

Crop Group 8, is fruits, including, for example, bananas and plantains; *citrus* fruits; pome fruits; stone fruits; berries; grapes; tropical fruits; miscellaneous fruits; and other fruits. *Citrus* fruits include, for example, orange, tangerine, mandarin, clementine, satsumas, lemon, lime, grapefruit, pomellow, bergamot, citron, chinotto, kumquat, and other *citrus* fruits. Pome fruits include, for example, apple, pear, quince, and other pome fruits. Stone fruits include, for example, apricot, cherry, peach, nectarine, plum, and other stone fruits. Berries include, for example, strawberry, raspberry, gooseberry, currant, blueberry, cranberry, blackberry, loganberry, mulberry, myrtle berry, huckleberry, dangleberry, and other berries. Tropical fruits include, for example, fig, persimmon, kiwi, mango, avocado, pineapple, date, cashew apple, papaya, breadfruit, carambola, chrimoya, durian, feijoa, guava, mombin, jackfruit, longan, mammee, mangosteen, naranjillo, passion fruit, rambutan, sapote, sapodilla, star apple, and other tropical fruits. Miscellaneous fruits include, for example, azarole, babaco, elderberry, jujube, litchi, loquat, medlar, pawpaw, pomegranate, prickly pear, rose hips, rowanberry, service-apple, tamarind, and tree-strawberry.

Crop Group 9 is fibers, including, for example, cotton, flax, hemp, kapok, jute, ramie, sisal, and other fibers from plants. In some embodiments, cotton plants are suitable.

Crop Group 10 is spices, including, for example, pepper, pimento, vanilla, cinnamon, nutmeg, mace, cardamon, cloves, anise, badian, fennel, ginger, bay leaves, dill seed, fenugreek seed, saffron, thyme, turmeric, and other spices.

Crop Group 11 is Fodder crops. Fodder crops are crops that are cultivated primarily for animal feed. Natural grasslands and pastures are included in crop group 11, whether they are cultivated or not. Fodder crops also include, for example, corn for forage, sorghum for forage, rye grass for forage, clover for forage, alfalfa for forage, other grasses for forage, green oilseeds for silage, legumes for silage, other crops for silage, cabbage for fodder, pumpkins for fodder, turnips for fodder, beets for fodder, carrots for fodder, swedes for fodder, other vegetables or roots for fodder, and other fodder crops.

Crop Group 12 is stimulant crops, including, for example, coffee, cocoa bean, tea, mate, other plants used for making infusions like tea, and other stimulant corps.

Crop Group 13 is tobacco and rubber and other crops, including, for example, chicory root, carob, hops, oil of citronella, peppermint, spearmint, other plant oils used in perfumery, food, and other industries, pyrethrum, tobacco, natural rubber, natural gums (including, for example, balata, cerea, chicle, guayule, gutta-percha, and jelutong), other resins (including, for example, copaiba, gum tragacanth, incense, myrrh, opopanax, mecca balsom, tolu balsam, and peru balsam), and vegetable waxes (including, for example, candelilla, carnauba, urucury, and palm wax).

In some embodiments, the present invention involves treatment of any non-*citrus* plant (i.e., any plant that is not in the genus *Citrus*). In other embodiments, the practice of the present invention is limited to the treatment of non-*citrus* plants.

Independently, in some of the embodiments in which apple trees are used in the practice of the present invention, the composition of the present invention contains no aminoethoxyvinylglycine, or, in some embodiments, no plant growth regulator of type II defined herein above; or, in some embodiments, no plant growth regulator that is not a cyclopropene. In other embodiments, no apple trees are used in the practice of the present invention. In some embodiments, no pome fruit trees are used in the practice of the present invention.

In some embodiments, plants are treated that are not members of the genus *Nicotiana*.

In some embodiments of the present invention, plants that are contacted with a composition of the present invention include one or more of corn or soybean or cotton or apple or pear or rice or wheat or tomato or grape or sorghum or plum or kiwi or walnut or almond or pecan or sunflower or oilseed rape or canola or barley or rye or triticale. In some embodiments of the present invention, plants that are contacted with a composition of the present invention include one or more of corn or soybean or cotton or apple or pear or rice or wheat or tomato or grape or sorghum. In some embodiments, plants that are contacted with a composition of the present invention include one or more of corn or soybean or cotton or wheat. In some embodiments, plants that are contacted with a composition of the present invention include corn. In some embodiments, plants that are contacted with a composition of the present invention include soybean. In some embodiments, plants that are contacted with a composition of the present invention include cotton. In some embodiments, plants that are contacted with a composition of the present invention include wheat.

In some embodiments, the amount of cyclopropene is chosen to be appropriate for the particular crop that is being treated. For example, in some of the embodiments in which the crop plants are corn or soybean, the amount of cyclopropene is 500 g/ha or less; or 250 g/ha or less; or 100 g/ha or less, or 50 g/ha or less. For another example, in some of the embodiments in which the crop plants are cotton, the amount of cyclopropene is 50 g/ha or more; or 100 g/ha or more; or 200 g/ha or more.

In some embodiments of the present invention, a group of plants is treated simultaneously or sequentially. One characteristic of such a group of plants is the crop yield, which is defined as the amount (herein called "crop amount") of useful plant parts collected from a defined group of plants. In one useful definition of the crop yield, the defined group of plants is the group that occupies a certain area of ground (this definition is often used when plants are growing in a contiguous group in a field). In another useful definition of the crop yield, the defined group of plants is a specific number of individually identified plants (this definition may be used for any group of plants, including, for example, plants in fields, in pots, in greenhouses, or any combination thereof).

The crop amount may defined in a variety of ways. In the practice of the present invention, the crop amount may be measured, for example, by any of the following methods: weight, volume, number of harvested plant parts, or biomass. Also contemplated are methods in which the crop amount is measured as the amount in the crop of a specific constituent (such as, for example, sugar, starch, or protein). Further contemplated are methods in which the crop amount is measured as the amount of a certain characteristic (such as, for example, redness, which is sometimes used to measure the amount of a crop of tomatoes). Additionally contemplated are methods in which the crop amount is measured as the amount of a specific portion of the harvested plant part (such as, for example, the number of kernels or the weight of kernels, which are sometimes used to measure the amount of a crop of corn; or the weight of lint, which is sometimes used to measure the amount of a cotton crop).

In some embodiments, the crop yield is defined as the crop amount per unit of area of land. That is, the land area from which the crop was harvested is measured, and the crop amount is divided by the land area to calculate the crop yield. For example, a crop amount measured as the weight of harvested plant parts would lead to a crop yield that is reported as a weight per area (for example, kilograms per hectare).

It is contemplated that, in some embodiments, the harvested plant parts that contribute to the crop amount are those plant parts that meet the minimum quality criteria that are appropriate for that type of plant part. That is, when plant parts are harvested from certain plants, the crop amount is, for example, the weight of the plant parts of acceptable quality that are harvested from those plants. Acceptable quality may be determined by any of the common criteria used by persons who harvest or handle the plant part of interest. Such criteria of acceptable quality of a plant part may be, for example, one or more of size, weight, firmness, resistance to bruising, flavor, sugar/starch balance, color, beauty, other quality criteria, or any combination thereof. Also contemplated as a criterion of quality, either alone or in combination with any of the foregoing criteria, is the time over which the plant part maintains its quality (as judged by any of the forgoing criteria).

In some embodiments of the present invention, treatment of a group of plants with the methods of the present invention will increase the crop yield of that group of plants, compared to the crop yield that would have been obtained from that group of plants if it had not been treated with the methods of the present invention. The increase in crop yield may be obtained in any of a wide variety of ways. For example, one way an increase in crop yield may be obtained is that each plant may produce a greater number of useful plant parts. As another example, one way an increase in crop yield may be obtained is that each useful plant part may have higher weight. As a third example, crop yield may increase when a larger number of potentially useful plant parts meets the minimum criteria for acceptable quality. Other ways of increasing the crop yield may also result from the practice of the present invention. Also contemplated are increases in crop yield that happen by any combination of ways.

Another contemplated benefit of practicing some embodiments of the present invention is that the general quality of the crop may be improved. That is, a crop produced by methods of the present invention may have a general or average level of quality higher than comparable crops produced without the methods of the present invention, as judged by the quality criteria appropriate for that crop. In some cases, such higher-quality crops may command higher prices when sold.

The improvement in crop yield caused by the practice of the present invention may arise by any mechanism. That is, the practice of the present invention, in some embodiments, may cause an improvement in some process of the plant's development, maturation, growth, or reproduction, and such improvement in such process may, in turn, cause improvement in crop yield. For example, the practice of the present invention may cause an improvement in any one or any combination of the following processes: synchronization of pollination (i.e., better agreement between the time period when a plant sheds pollen and the time period when that plant is able to receive the pollen and become fertilized), photosynthesis, nitrogen accumulation, leaf senescence, or late-season production of green leaves. In some of the embodiments where photosynthesis is improved, the improvement in photosynthesis can be observed as increased assimilation of carbon dioxide. Independently, the improvement in crop yield may, in some embodiments, occur because of improvement in disease resistance or drought resistance or frost resistance or heat resistance or a combination thereof.

In some crops (such as, for example, corn), it is contemplated that drought resistance and the resultant improvement in crop yield arise because the practice of the present invention causes stomatal closure, which gives the plant its resistance to drought. Independently, some crops (such as, for example, wheat) experience improved frost tolerance when used in the practice of the present invention. Independently, some crops (such as, for example, wheat and grapes) experience improved resistance to disease when used in the practice of the present invention.

Independently, in some embodiments, improvement in crop yield may occur because of a delay in the dropping of one or more of leaves, flowers, or fruiting structures (such as, for example, pods, bolls, or the fruit itself).

Independently, in some embodiments, improvement in crop yield may occur because of enhanced root nodulation, which sometimes occurs in certain crops such as, for example, soybeans.

Whether or not the practice of the present invention results in improvement in one or more of the above-mentioned processes, in some embodiments the practice of the present invention leads to improvement in one or more of the following: biomass volume, biomass quality, increased fruit, increased fruit size (when desired), decreased fruit size (when desired), harvest timing (advanced or delayed, as desired), reduced fruit drop, decreased cell turgor, decreased russeting, lowered stress response, lowered wounding response, reduced storage disorders in harvested plant parts, increased shelf life of harvested plant parts, apical dominance, abscission prevention, senescence prevention, yellowing prevention, improved vigor during growth, improved vigor during transmit, improved vigor during transplant, and combinations thereof.

In some embodiments, an improvement in crop yield is evident at the time of harvest, such as, for example, when the improvement is an increase in weight of crop per unit area of land.

Independently, in some embodiments, an improvement in crop yield is observed some time after the crop has been in storage. That is, in some cases, the crop yield is measured as the amount of high-quality crop that is delivered to the retail market after storage. It is contemplated that some embodiments of the present invention involve pre-harvest contacting of crop plants resulting in crop that can be put in storage after harvest and then come out of storage with higher quality than previously obtainable. For example, apples sometimes develop an undesirable clear appearance in the flesh of the fruit known as "water core" while still on the tree. Water core, when present, can persist during storage after harvest. In some embodiments of the present invention, apple trees are contacted with a composition of the present invention prior to harvest, and the resulting crop of apples has an improved resistance to developing water core. Similarly, some varieties of apples (such as, for example, fuji apples) develop undesirable red spots known as "staining" during storage after harvest. In some embodiments of the present invention, apple trees are contacted with a composition of the present invention prior to harvest, and the resulting crop of apples has an improved resistance to developing red spots during storage.

It is to be understood that for purposes of the present specification and claims that the range and ratio limits recited herein can be combined. For example, if ranges of 60 to 120 and 80 to 110 are recited for a particular parameter, then the ranges of 60 to 110 and 80 to 120 are also contemplated. For another example, if minimum values for a particular parameter of 1, 2, and 3 are recited, and if maximum values of 4 and 5 are recited for that parameter, then it is also understood that the following ranges are all contemplated: 1 to 4, 1 to 5, 2 to 4, 2 to 5, 3 to 4, and 3 to 5.

EXAMPLES

In the Examples below, the following materials were used:
Powder 1=powder containing 3.8% 1-MCP by weight, available as AFXRD-038 from Rohm and Haas Co.
Powder 2=powder containing 2.0% 1-MCP by weight, available as AFXRD-020 from Rohm and Haas Co.
Adjuvant 1=oil "AF-400," which contains
    PureSpray Spray Oil 10, available from Petro Canada Co., and
    Aerosol™ OT surfactant, available from Cytec Industries, and
    Tomadol™ surfactant, available from Tomah Co.
NAA=1-naphthaleneacetic acid
AVG=aminoethoxyvinylglycine
In the following examples, these procedures were used:
Spray tank was filled with approximately two-thirds of the total volume of water required. The amount of Powder 1 or Powder 2 was weighed according to the rate and total volume of spray being prepared. The appropriate amount of was calculated to give 1% v/v of total spray volume. Adjuvant 1 was added to the spray tank, which was agitated until the mixture turned milky white. Powder 1 or Powder 2 was added to the spray container, which was then gently (not vigorously) agitated. The remaining water was added, making sure all of the powder was wet and washed off of the sides of the tank (if any had deposited there). The spray tank was then swirled or stirred for at least two minutes (2-5 minutes) to ensure good mixing. Between 5 and 60 minutes thereafter, plants were sprayed with the mixture.

Flat fan nozzles were used, producing droplet size of 100 to 500 micrometers. Spray rate of mixture was 500 liter per hectare. Backpack sprayer was used. Spraying was performed before 10:00 am.

In the following Examples, these abbreviations are used: ha for hectare, mT for metric ton, AI for 1-MCP, and wt for weight.

Example 1

Corn General

Corn of hybrid variety FR1064X LH185 was planted, 72,000 plants per hectare, treated with nitrogen at 22 kg/ha (120 lb. per acre). Powder 1 was used. Treatment time (ie, developmental stage at which treatment was performed), treatment amounts (grams of AI per hectare), and results were as follows. The simple measure of yield is reported as metric ton (mT) per hectare. Other measures of yield are also shown. Treatments lead to increase in yield by one or more measures.

| Treatment Stage | Amount (g/ha) | Yield (mT/ha) | Kernel wt (mg) | Kernel no.[1] | Protein %[2] | Starch %[2] | Oil %[2] |
|---|---|---|---|---|---|---|---|
| UTC[3] | 0 | 1.64 | 248 | 444 | 7.8 | 71.7 | 4.6 |
| V12 | 10 | 1.80[4] | 266[4] | 471 | 7.7 | 71.7 | 4.6 |
| V12 | 25 | 1.84[4] | 270[4] | 495[4] | 7.5 | 72.0 | 4.6 |
| VT | 10 | 1.86[4] | 267[4] | 480 | 7.5 | 72.1[4] | 4.5 |
| VT | 25 | 1.87[4] | 277[4] | 451 | 7.7 | 71.7 | 4.6 |
| R3 | 10 | 1.81[4] | 265[4] | 454 | 7.3 | 72.2 | 4.6 |
| R3 | 25 | 1.82[4] | 265[4] | 471 | 7.6 | 72.1 | 4.7 |
| V12, VT | 10 | 1.82[4] | 263[4] | 459 | 7.6 | 71.9 | 4.5 |
| VT, R3 | 10 | 1.72 | 271[4] | 437 | 7.7 | 71.6 | 4.8[4] |
| V12, VT, R3 | 10 | 1.70 | 259 | 464 | 7.2[4] | 72.4[4] | 4.6 |

Notes:
[1] number of kernels per plant
[2] weight of protein (or starch or oil) as a percent based on the weight of the kernels.
[3] un-treated control. No AI was used.
[4] statistically distinct from the result obtained in the UTC sample

Example 2

Cotton Lint

Using methods similar to those of Example 1, cotton was also tested. Each treated group of plants was treated either two or three times, as follows:

| Treatment Type | First Treatment | Second Treatment | Third Treatment |
|---|---|---|---|
| PHS 2 | soon after appearance of pinhead squares | 14 days after first treatment | none |
| PHS 3 | soon after appearance of pinhead squares | 14 days after first treatment | 28 days after first treatment |
| EB 2 | soon after appearance of early bloom | 14 days after first treatment | none |
| EB 3 | soon after appearance of early bloom | 14 days after first treatment | 28 days after first treatment |

The crop yield was assessed as the weight of lint per hectare. Treatment types, treatment amounts (grams of AI per hectare), and results were as follows. Many of the treatments lead to improvements in the yield of lint.

| Amount (g/ha) | Type | Lint (kg/ha) |
|---|---|---|
| 250 | PHS 2 | 230.6 |
| 250 | PHS 3 | 231.8 |
| 250 | EB 2 | 245.3 |
| 250 | EB 3 | 250.2 |
| 500 | PHS 2 | 257.6 |
| 500 | PHS 3 | 262.0 |
| 500 | EB 2 | 234.2 |
| 500 | EB 3 | 261.3 |
| 1250 | PHS 2 | 253.9 |
| 1250 | PHS 3 | 241.4 |
| 1250 | EB 2 | 235.0 |
| 1250 | EB 3 | 260.7 |
| 0 | UTC[3] | 228.0 |
| 0 | Adjuvant 1 only | 245.1 |

Example 3

Golden Delicious Fruit Drop

Using methods similar to those of Example 1, Golden Delicious apple trees were sprayed one week before the apples would normally be harvested for commercial use. The apples were left on the trees to observe postharvest drop. The spray containing Powder 1 was used to give 375 gram of AI per hectare. NAA was used at 20 ppm, and AVG was used at 125 ppm. Trees treated with Powder 1 showed the least fruit drop and thus the best crop yield. Results (number of dropped fruit per tree) were as follows:

| Day[5] | UTC[3] | NAA treated | AVG treated | Powder 1 treated |
|---|---|---|---|---|
| 0 | 0 | 0 | 0 | 0 |
| 7 | 18 | 5 | 5 | 4 |
| 62 | 30 | 11 | 11 | 9 |
| 21 | 45 | 20 | 23 | 15 |
| 28 | 115 | 65 | 35 | 20 |
| 35 | 195 | 118 | 45 | 39 |

[5] Number of days after treatment

Example 4A

Scarletspur Delicious Apples and Water Core

Using methods similar to those of Example 1, Scarletspur Delicious apple trees were sprayed immediately before commercial harvest timing. The spray containing Powder 1 was used to give 375 gram of AI per hectare. The harvested apples were evaluated for the presence of watercore.

The following table shows the % of apples, based on the number of apples in storage, that show no watercore as a function of days after harvest ("days AH"). The treated apples show a comparable or higher percentage of watercore-free apples.

| Days AH | UTC (%) | Treated (%) |
|---|---|---|
| 4 | 98 | 95 |
| 8 | 98 | 98 |
| 12 | 82 | 98 |
| 15 | 70 | 98 |
| 19 | 66 | 95 |
| 24 | 40 | 98 |
| 29 | 20 | 98 |
| 34 | 10 | 42 |

Example 4B

Fuji Apples and Staining

Fuji apple trees were sprayed prior to harvest either one or two times, with spray containing 250 ppm of 1-MCP. Each spraying provided treatment of approximately 211 g/ha (520 g/acre). After harvesting and storage, the apples were inspected for staining. The percent of apples that showed staining was as follows:

| Treatment | % Staining |
| --- | --- |
| Untreated | 12 |
| 1 spray application | 8.5 |
| 2 spray applications | 3 |

Example 5

Wheat Resistance to Frost and Disease

Using methods similar to those of Example 1, wheat was sprayed at stage F10.5. Frost damage was assessed by examining the portion of the seed head damaged; the percentage of barren husks is reported. Damage from *fusarium* disease was assessed as a percentage of seed heads damaged by the disease organism. The following table shows that the treated wheat showed higher yield, lower frost damage, and lower disease damage.

| Treatment (AI g/ha) | Yield (kg dry weight/ha) | Frost Damage (%) | Disease Damage (%) |
| --- | --- | --- | --- |
| 0 | 3890 | 21 | 6 |
| 10 | 4458 | 6 | 0.5 |
| 25 | 4522 | 3 | 3 |

Example 6

Soybean Crop Yield Increase

Soybean plants were treated using methods similar to those of Example 1. Treatment was performed when the plants were at one or more of the following growth stages: R2, R3, and R5.5. The results are shown below:

| Number | Dosage (g/ha) | Timing | Yield (kg/ha) | Protein % |
| --- | --- | --- | --- | --- |
| 1 | Untreated | | 3607.20 | 36.93 |
| 2 | Oil only | R2, R3, and R5.5 | 3661.56 | 37.02 |
| 3 | 1 | R2 | 3691.44 | 37.88 |
| 4 | 1 | R3 | 3795.48 | 37.89 |
| 5 | 1 | R5.5 | 3659.76 | 38.25 |
| 6 | 1 | R2 and R3 | 3786.48 | 37.85 |
| 7 | 1 | R2 and R5.5 | 3704.04 | 38.45 |
| 8 | 1 | R3 and R5.5 | 3763.80 | 38.75 |
| 9 | 1 | R2, R3, and R5.5 | 3955.68 | 38.4 |
| 10 | 10 | R2 | 3671.64 | 37.67 |
| 11 | 10 | R3 | 3757.68 | 38.64 |
| 12 | 10 | R5.5 | 3721.32 | 38.32 |
| 13 | 10 | R2 and R3 | 3872.84 | 38.27 |
| 14 | 10 | R2 and R5.5 | 3817.80 | 38.63 |
| 15 | 10 | R3 and R5.5 | 3791.52 | 38.3 |
| 16 | 10 | R2, R3, and R5.5 | 4119.48 | 37.87 |
| 17 | 30 | R2 | 3702.24 | 38.08 |
| 18 | 30 | R3 | 3747.24 | 38.33 |
| 19 | 30 | R5.5 | 3817.80 | 37.58 |
| 20 | 30 | R2 and R3 | 4118.76 | 36.73 |
| 21 | 30 | R2 and R5.5 | 3844.44 | 38.56 |
| 22 | 30 | R3 and R5.5 | 3946.68 | 37.87 |
| 23 | 30 | R2, R3, and R5.5 | 4347.00 | 37.48 |
| 24 | Untreated | | 3687.67 | 36.87 |
| 25 | Exaggerated 1 | every 2 weeks | 3923.64 | 38.62 |
| 26 | Exaggerated 2 | every 2 weeks | 4167.00 | 37.89 |

Treatment improved both the yield of soybeans and the protein content of the harvested beans.

We claim:

1. A method for improving the yield of a crop produced by a plurality of wheat plants, wherein said method comprises contacting said wheat plants at least one time with a liquid composition comprising 1-methylcyclopropene (1-MCP), a solvent and at least one adjuvant selected from the group consisting of surfactants, alcohols, oils, extenders, pigments, fillers, binders, plasticizers, lubricants, wetting agents, spreading agents, dispersing agents, stickers, adhesives, defoamers, thickeners, transport agents, and emulsifying agents,
    wherein said contacting is performed during the F10.5 growth stage, and
    wherein the contacting is performed at a rate of 1 to 25 g of said 1-methylcyclopropene (1-MCP) per hectare.

2. The method of claim 1, wherein improving said crop yield comprises improving disease resistance or frost resistance or both of said wheat plants.

3. The method of claim 1, wherein said improving said crop yield comprises one or more of improving the disease resistance of said plants or improving the drought resistance of said slants or improving the frost resistance of said slants or improving the heat resistance of said plants or improving the photosynthesis process of said plants or improving the synchronization of pollination processes of said plants or delaying leaf senescence of said plants or improving the nitrogen accumulation of said plants or improving the production of green leaves late in the growing season of said plants or enhancing the root nodulation of said plants or inhibiting the dropping of one or more of leaves, flowers, or fruiting structures from said plants.

4. The method of claim 1, wherein said solvent comprises water.

5. The method of claim 1, wherein said method improves said yield by improving the heat resistance of said plants.

6. The method of claim 1, wherein said method improves said yield by improving the drought resistance of said plants.

7. The method of claim 1, wherein said contacting is performed by spraying said liquid composition.

* * * * *